United States Patent
Coveley et al.

(10) Patent No.: US 8,145,546 B2
(45) Date of Patent: Mar. 27, 2012

(54) SYSTEM AND METHOD FOR TRACKING INVENTORY

(75) Inventors: Michael E. Coveley, North York (CA); Srdjan Milutinovic, Mississauga (CA)

(73) Assignee: cStar Technologies Inc., Ontario (CA)

( * ) Notice: Subject to any disclaimer, the term of this patent is extended or adjusted under 35 U.S.C. 154(b) by 0 days.

(21) Appl. No.: 12/656,069

(22) Filed: Jan. 14, 2010

(65) Prior Publication Data
US 2011/0000964 A1     Jan. 6, 2011

Related U.S. Application Data

(63) Continuation of application No. 10/853,251, filed on May 26, 2004, now abandoned.

(51) Int. Cl.
*G06Q 10/00* (2006.01)
*G06F 19/00* (2011.01)
(52) U.S. Cl. ............................................. 705/28; 705/3
(58) Field of Classification Search ...................... 705/28
See application file for complete search history.

(56) References Cited

U.S. PATENT DOCUMENTS

| | | | |
|---|---|---|---|
| 4,419,734 A | 12/1983 | Wolfson et al. | |
| 4,967,928 A | 11/1990 | Carter | |
| 5,512,887 A * | 4/1996 | McAllister | 340/5.65 |
| 5,671,362 A | 9/1997 | Cowe et al. | |
| 5,790,409 A | 8/1998 | Fedor et al. | |
| 6,131,399 A * | 10/2000 | Hall | 62/127 |
| 6,418,416 B1 | 7/2002 | Rosenburg et al. | |
| 6,509,826 B1 | 1/2003 | Loftus | |
| 6,604,017 B1 * | 8/2003 | Richardson et al. | 700/223 |
| 6,611,806 B1 | 8/2003 | Harvey | |
| 7,003,495 B1 | 2/2006 | Burger et al. | |
| 7,032,818 B2 | 4/2006 | Thomas et al. | |
| 7,349,858 B1 * | 3/2008 | McGrady et al. | 705/3 |
| 2002/0067261 A1 | 6/2002 | Kucharczyk et al. | |
| 2002/0070846 A1 | 6/2002 | Bastian et al. | |
| 2003/0083964 A1 | 5/2003 | Horwitz et al. | |
| 2003/0212602 A1 | 11/2003 | Schaller | |
| 2003/0225596 A1 * | 12/2003 | Richardson et al. | 705/2 |

FOREIGN PATENT DOCUMENTS

| | | |
|---|---|---|
| EP | 0 572 119 | 12/1993 |
| FR | 2 774 749 | 8/1999 |
| JP | 60-208576 | 10/1985 |

OTHER PUBLICATIONS

Foreign Search Report issued on Aug. 13, 2004.

* cited by examiner

*Primary Examiner* — Garcia Ade
(74) *Attorney, Agent, or Firm* — Harness, Dickey & Pierce (57) ABSTRACT

An inventory-tracking unit associated with a storage unit holding items to be dispensed includes a card reader to read an access card issued to a user and a recorder to record data from items removed from the storage unit. A processor communicates with a sensor in the storage unit and with the card reader and recorder. The sensor provides item data to the processor that is associated with items removed from the storage unit. The processor compares item data received from the sensor with the data recorded by the recorder to detect coincidence. The processor generates a transaction upon coincidence of item data received from the sensor with the recorded data. A communications interface transmits the transaction to a remote site.

24 Claims, 7 Drawing Sheets

SYSTEM AND METHOD FOR TRACKING INVENTORY

PRIORITY STATEMENT

This application is a continuation application of U.S. patent application Ser. No. 10/853,251, filed on May 26, 2004 now abandoned, and claims the associated benefit under 35 U.S.C. §120. The entire contents of parent U.S. patent application Ser. No. 10/853,251, entitled "SYSTEM AND METHOD FOR TRACKING INVENTORY", are incorporated herein by reference.

BACKGROUND

1. Field

The present invention relates generally to inventory management and in particular to a system and method for tracking inventory and to an inventory-tracking unit.

2. Description of Related Art

Inventory control is a primary concern for product retailers so that excess and insufficient inventory situations are avoided. Within a mortar and bricks environment, inventory is controlled by counting existing inventory at physical locations. Controlling inventory in this manner is however much more difficult and in fact impractical in environments where inventory is dispensed through stocked vending machines that are distributed over a large geographical area.

To deal with inventory control in these environments, service personnel are dispatched along service routes according to pre-set schedules so that the vending machines can be checked for inventory levels and proper operation. As will be appreciated, during a service route all vending machines along the service route are checked. In many instances, the checks reveal that the vending machines are operating properly and hold sufficient inventory. As a result, the checks are unnecessary. In other instances, the checks reveal that the vending machines have malfunctioned and/or are depleted of inventory, resulting in potential lost sales especially if delays exist between checks.

A similar problem exists in the medical supply environment where medical, surgical, biological and/or pharmaceutical supplies are stored in refrigeration units distributed throughout medical, research and/or educational facilities located at different geographical locations. In the past, dispatching medical supplies through these refrigeration units has been based on the honor system. Users removing supplies from refrigeration units are expected to list the removed supplies on charts posted on the refrigeration units so that supply usage can be tracked and costs assigned in the appropriate manner.

As will be appreciated, inventory control in this medical supply environment suffers similar problems to those encountered in the vending machine environment discussed above. Routine checks of all refrigeration units must be carried out to determine the inventory level and operating status of the refrigeration units. In many cases the checks are either unnecessary or late. The latter condition can be particularly problematic in the case where a refrigeration unit fails and the temperature within the refrigeration unit rises to a point where the inventory is spoiled. Inventory shrinkage is also a problem in the medical supply environment. In many instances, users removing supplies from the refrigeration units fail to record accurately the removed items. As a result, costs for the missing inventory cannot be assigned. As will be appreciated, improvements in inventory control in these types of environments are desired.

It is therefore an object of the present invention to provide a novel system and method for tracking inventory and a novel inventory-tracking unit.

SUMMARY

According to one aspect of the present invention there is provided an inventory-tracking unit associated with a storage unit holding items to be dispensed comprising:
a card reader to read an access card issued to a user;
a recorder to record data from items removed from said storage unit;
a processor communicating with a sensor in said storage unit and with said card reader and recorder, said sensor providing item data to said processor that is associated with items removed from said storage unit, said processor comparing item data received from said sensor with data recorded by said recorder to detect coincidence, said processor generating a transaction upon coincidence of item data received from said sensor with said recorded data; and
a communications interface to transmit said transaction to a remote site.

In one embodiment, the communications interface transmits the transaction over a wireless communications link, the recorder is a barcode scanner, the card reader is designed to read a magnetic stripe on an access card and the storage unit is a refrigeration unit. A housing accommodates the card reader, barcode scanner, processor and communications interface. The housing is coupled to the storage unit and the processor is wired to the sensor. During access of the storage unit, the card reader locks the access card therein until the item data received from the sensor is coincident with the recorded data.

In one embodiment, the inventory-tracking unit further comprising a locking mechanism coupled to the storage unit to inhibit access to items held therein. The locking mechanism is conditioned by the processor to a disengaged state to permit access to items held in the storage unit when a valid access card is read by the card reader. The processor communicates with at least one diagnostic sensor associated with the storage unit and transmits an alarm event to the remote site in response to alarm condition input received from the at least one diagnostic sensor.

According to another aspect of the present invention there is provided an inventory-tracking system comprising:
a remote site; and
at least one inventory-tracking unit associated with storage unit holding items to be sensed, said inventory-tracking unit comprising:
an inventory-tracking unit associated with a storage unit holding items to be dispensed comprising:
a card reader to read an access card issued to a user;
a recorder to record data from items removed from said storage unit;
a processor communicating with a sensor in said storage unit and with said card reader and scanner, said sensor providing item data to said processor that is associated with items removed from said storage unit, said processor comparing item data received from said sensor with data recorded by said recorder to detect coincidence, said processor generating a transaction upon coincidence of item data received from said sensor with said recorded data; and
a communications interface to transmit said transaction to a remote site.

The present invention provides advantages in that the inventory-tracking unit can be easily retrofitted to existing refrigeration units thereby to permit existing refrigeration units to be upgraded so that inventory therein can be remotely monitored and tracked over a wireless communications link. Since the inventory-tracking unit controls access to the inventory within the refrigeration unit, distribution of restricted inventory can be accurately controlled thereby to inhibit inventory loss through inventory expiry and/or shrinkage.

The present invention also provides advantages in that since inventory removed from the refrigeration unit is tracked in real time, inventory within the refrigeration unit can be managed to avoid item "sell-out" conditions. Statistical information concerning inventory use can also be easily generated allowing inventory stocking procedures to be adjusted to meet inventory demand. In addition, if the refrigeration unit suffers a failure and the temperature within the refrigeration unit rises above a threshold temperature, since the operating state of the refrigeration unit is remotely monitored service personnel can be dispatched quickly to avoid inventory spoilage.

BRIEF DESCRIPTION OF THE DRAWINGS

Embodiments of the present invention will now be described more fully with reference to the accompanying drawings in which.

DETAILED DESCRIPTION OF EXAMPLE EMBODIMENTS

Figure 1:
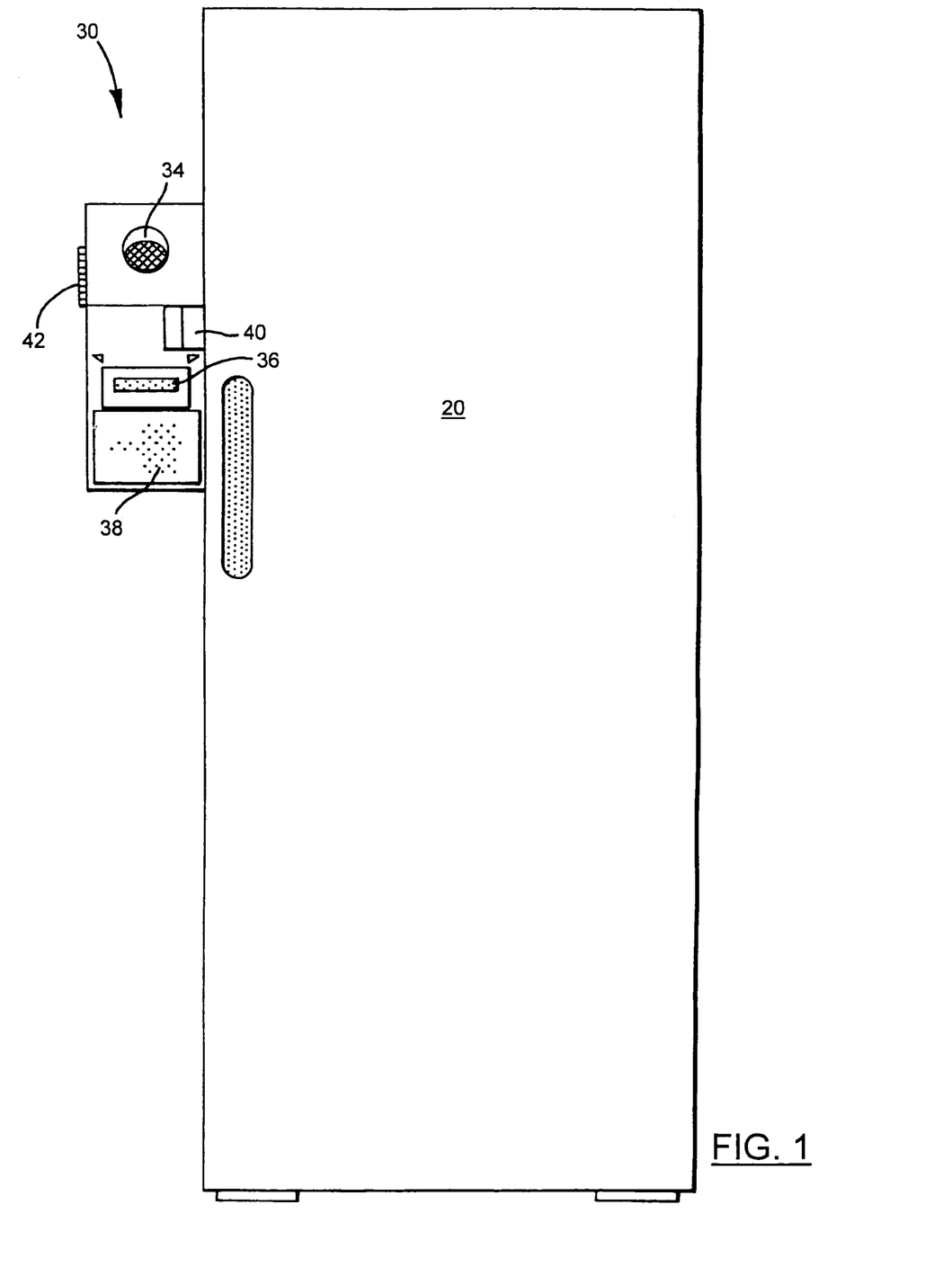
FIG. 1 is a front elevation view of a refrigeration unit in combination with an inventory-tracking unit in accordance with the present invention.
Figure 2:
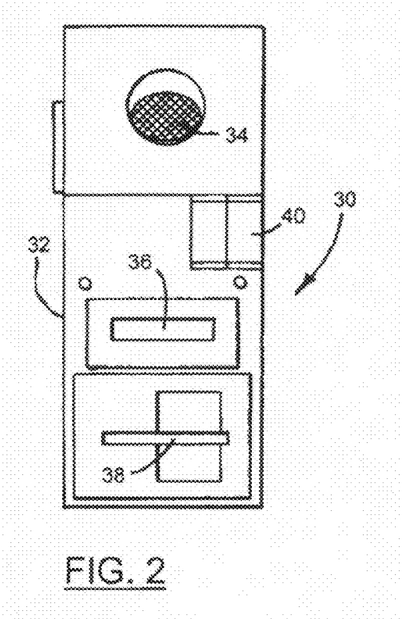
FIG. 2 is a front elevation view of the inventory-tracking unit of FIG. 1.
Figure 3:
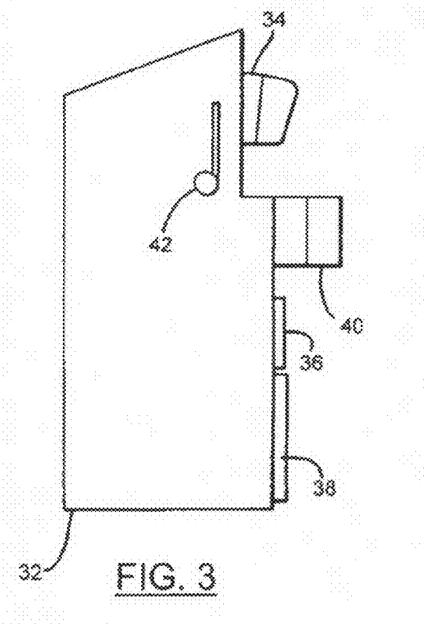
FIG. 3 is a left side elevation view of the inventory-tracking unit of FIG. 1.
Figure 4:
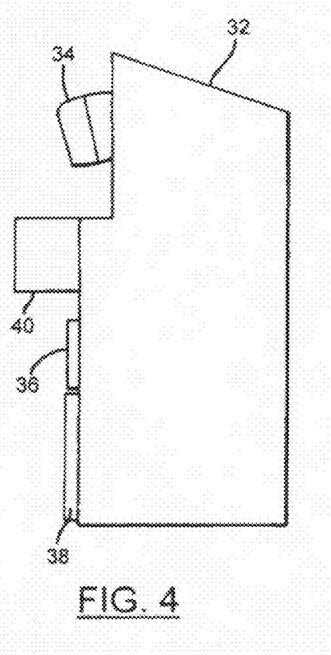
FIG. 4 is a right side elevation view of the inventory-tracking unit of FIG. 1.
Figure 5:
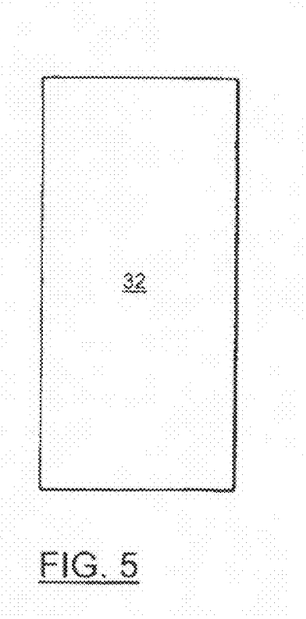
FIG. 5 is a rear elevation view of the inventory-tracking unit of FIG. 1.
Figure 6:
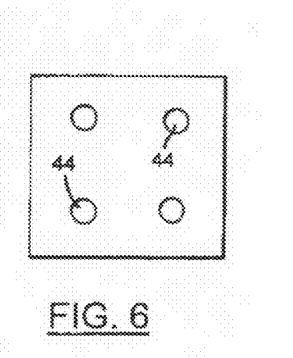
FIG. 6 is a top plan view of the inventory-tracking unit of FIG. 1.
Figure 11:
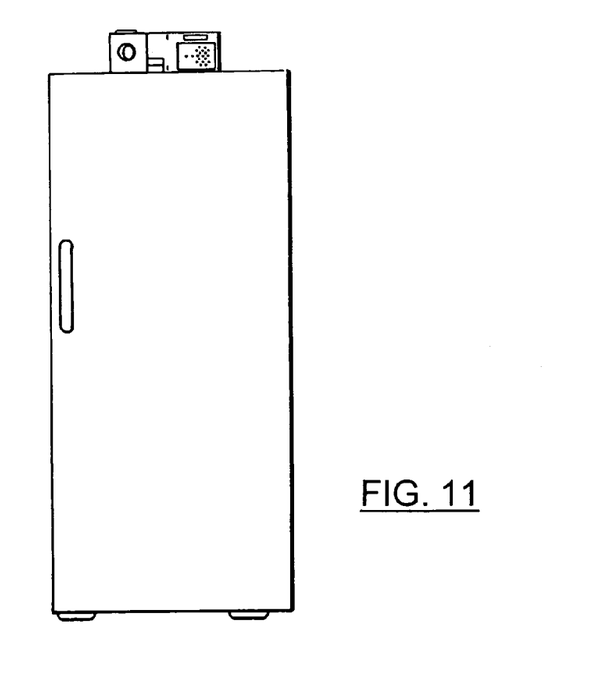
FIG. 11 is a front elevation view of a refrigeration unit in combination with a top mounted inventory-tracking unit.

Turning now to FIG. 1, a refrigeration unit such as a freezer in which medical, surgical, biological and/or pharmaceutical supplies (hereinafter referred to as "medical supplies") are stored, is shown and is generally identified by reference numeral 20. An inventory-tracking unit 30 is coupled to one side of the refrigeration unit 20 to track inventory removed from the refrigeration unit. The inventory-tracking unit 30 may alternatively be mounted on the top of the refrigeration unit 20 as shown in FIG. 11.

The refrigeration unit 20 for the most part is standard and receives power from a conventional 120 volt AC power source via an electrical cord. A door light switch is provided in the refrigeration unit 20 to sense when the door of the refrigeration unit is in an open or closed condition. As is known, when the door of the refrigeration unit 20 is opened, the door light switch closes a circuit causing an internal light within the refrigeration unit 20 to illuminate. An internal sensor antenna of the acoustic or electromagnetic type (not shown) is accommodated within the rubber seal surrounding the door frame of the refrigeration unit 20 to sense tagged items being placed in or removed from the refrigeration unit. A temperature sensor in the form of a thermistor is also provided in the refrigeration unit 20 to sense when the temperature within the refrigeration unit 20 rises above a threshold temperature.

FIGS. 2 to 6 better illustrate the physical layout of the inventory-tracking unit 30. As can be seen inventory-tracking unit 30 includes a housing 32 that is secured to the side of the refrigeration unit 20 by a plurality of suitable fasteners (not shown). The front face of the housing includes a barcode scanner or reader 34, a display 36 and a card reader 38. A spring-loaded solenoid door lock 40 is also provided on the front face of the housing 32 and is actuable to engage and disengage the door of the refrigeration unit to control entry into the refrigeration unit 20. An antenna 42 is provided on one side of the housing 32 to allow the inventory-tracking unit 30 to communicate with a remote site over a wireless communication link as will be described. Ventilation holes 44 are provided in the top of the housing 32 to allow air to circulate within the housing 32 thereby to dissipate heat.

Figure 7:
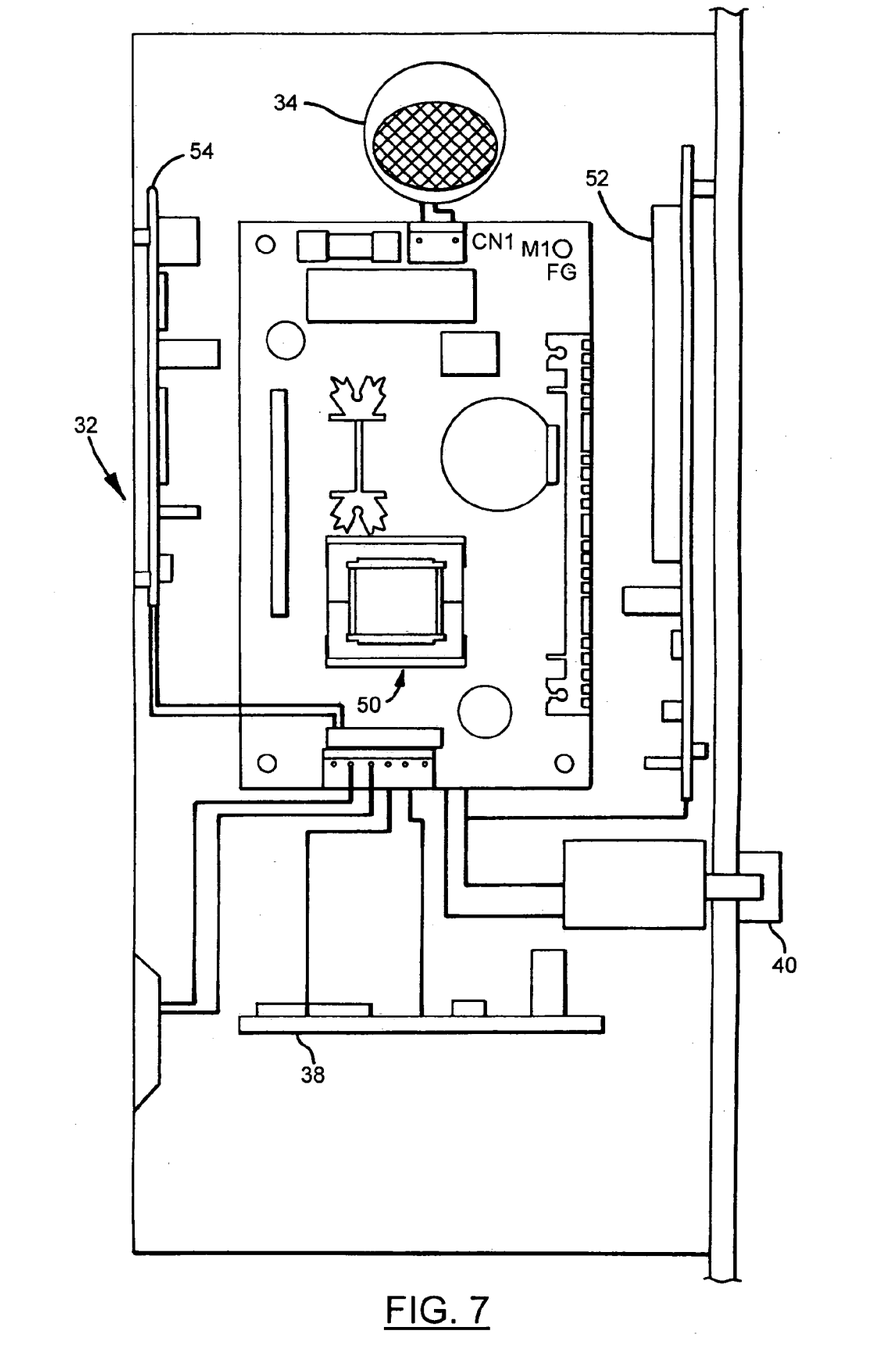
FIG. 7 is a front elevation view of the interior of the inventory-tracking unit of FIG. 1.

Turning now to FIG. 7, the integrated internal physical layout of the inventory-tracking device 30 is illustrated. The inventory-tracking device 30 includes a main control board 50 that communicates with the barcode scanner 34, the display 36, the card reader 38 and the solenoid door lock 40. The main control board 50 also communicates with a modem 52 that is coupled to the antenna 42 as well as with a multi-drop bus (MDB) board 54. An audio siren 56 is also coupled to the main control board 50.

Figure 8:
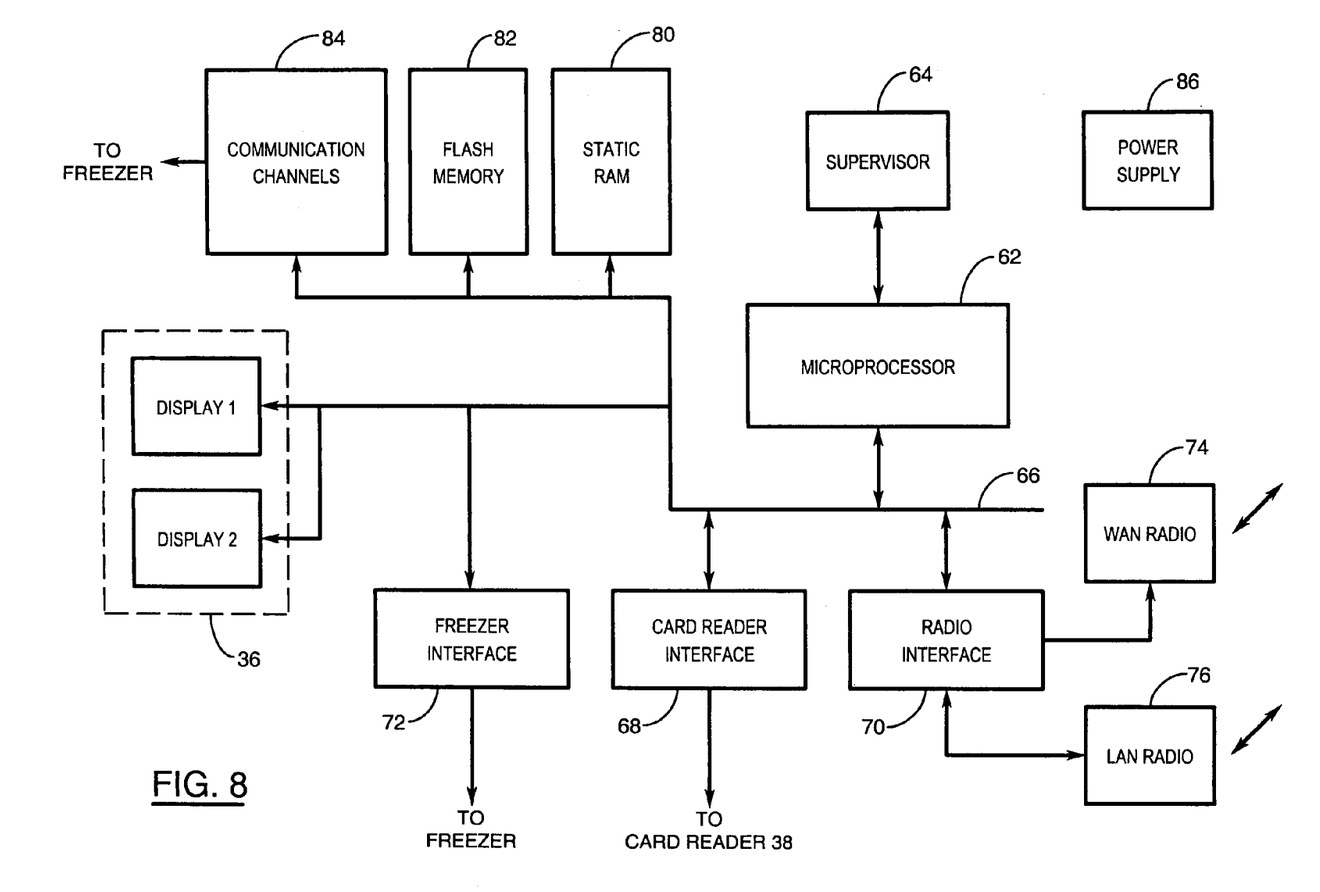
FIG. 8 is a block diagram of internal circuitry within the inventory-tracking unit of FIG. 1.

The circuitry on the main control board 50 and the multi-drop bus board 54 is illustrated in FIG. 8 and is generally identified by reference numeral 60. As can be seen, circuitry 60 includes a central processing unit (CPU) 62 having a real-time clock. CPU 62 communicates with a microprocessor supervisor 64 and with a plurality of interfaces via a databus 66, namely a card reader interface 68, a radio interface 70, and a freezer interface 72. Card reader interface 68 is coupled to the card reader 38. Radio interface 70 is coupled to a wide area network (WAN) radio transceiver 74 and/or to a local area network (LAN) radio transceiver 76. The transceivers 74 and 76 communicate with the antenna 42 thereby to permit wireless communications. The freezer interface 72 is coupled to the solenoid door lock 40.

CPU 62 further communicates with static random access memory (RAM) 80, flash memory 82 and communications interface 84 via the databus 66. The communications interface 84 communicates with the internal sensor antenna within the refrigeration unit 20. The display 36 is also coupled to the databus 66 and communicates with the CPU 62. An on-board power supply 86 provides the necessary power for operation of the inventory-tracking unit 30. On-board power supply 86 is coupled to the electrical cord of the refrigeration unit 20 via an interconnecting harness (not shown). CPU 62 also receives conductors coupled to the door light switch within the refrigeration unit 20 via the interconnecting harness allowing a time stamp to be generated when the door of the refrigeration unit 20 is opened and then closed.

Figure 9:
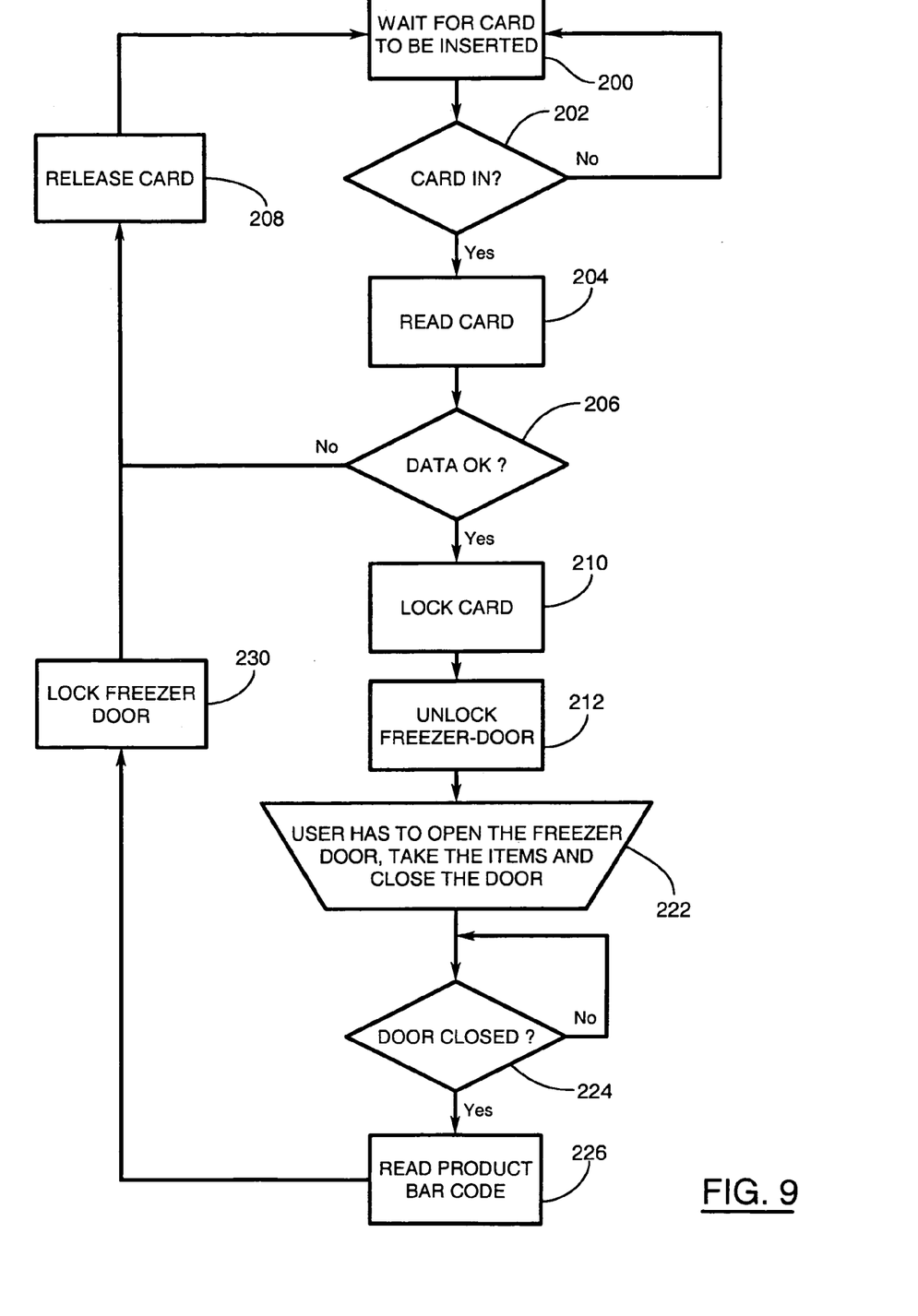
FIG. 9 is a flowchart showing the steps performed by the inventory-tracking unit during accessing of the refrigeration unit.

The operation of the inventory-tracking unit 30 will now be described with particular reference to FIG. 9. When a user wishes to gain access to the refrigeration unit 20, the user inserts their access card into the card reader 38. When the card reader 38 detects the inserted card (step 202), the magnetic stripe on the access card is read (step 204) and the read card data is conveyed to the CPU 62 via the databus 66. The CPU 66 in turn compares the read card data with a list of authorized users to determine if the card is valid (step 206). If the read card data is determined to be invalid, the user is denied access to the refrigeration unit 20. The access card is ejected from the card reader 38 (step 208) and the card reader returns to a ready state waiting for another access card to be inserted therein (step 200). At step 206, if the read card data is determined to be valid, the CPU 62 signals the card reader 38 to lock the access card therein (step 210). The CPU 62 also signals the solenoid door lock 40 via the freezer interface 72 causing the solenoid door lock to disengage the door of the refrigeration unit 20 (step 212). With the door of the refrigeration unit 20 unlocked, the user is able to open the refrigeration unit 20 thereby to gain access to supplies therein.

When the user opens the door of the refrigeration unit and the door light switch closes the circuit to illuminate the interior light within the refrigeration unit 20, a signal is conveyed to the CPU 62. The CPU 62 in turn generates a time stamp using the real-time clock allowing the time the refrigeration unit 20 is in an open condition to be accurately tracked. As the user begins removing items from the refrigeration unit 20, the tag on each removed item is detected by the internal sensor antenna. The internal sensor antenna in turn signals the CPU 62 via the communications interface 84 and databus 66 allowing the CPU 62 to maintain a count of the removed items (step 222).

When the door of the refrigeration unit 20 is closed, the CPU 62 conditions the barcode scanner 34 to a ready state and ends the time stamp (step 224). As a result, the length of time each user maintains the refrigeration unit 20 opened can be monitored. Extended door open conditions that may cause undesired temperature changes within the refrigeration unit 20 can also be detected. With the barcode scanner 34 enabled, the user is required to pass the removed items beneath the barcode scanner 34 so that the barcodes on the removed items can be scanned. After each barcode is scanned, the barcode scanner 34 conveys the scanned barcodes to the CPU 62 allowing the CPU 62 to maintain a list of the scanned items (step 226). When the number of scanned items is equal to the removed item count, the CPU 62 signals the solenoid door lock 40 via the freezer interface 72 causing the solenoid door lock 40 to engage the door of the refrigeration unit 20 (step 230). The access card is then ejected from the card reader 38 (step 208) and the card reader returns to a ready state waiting for another access card to be inserted therein (step 200). As will be appreciated, since a count of removed items is maintained and compared with the list of scanned barcodes, accurate transactions involving inventory within the refrigeration unit 20 can be maintained.

Figure 10:
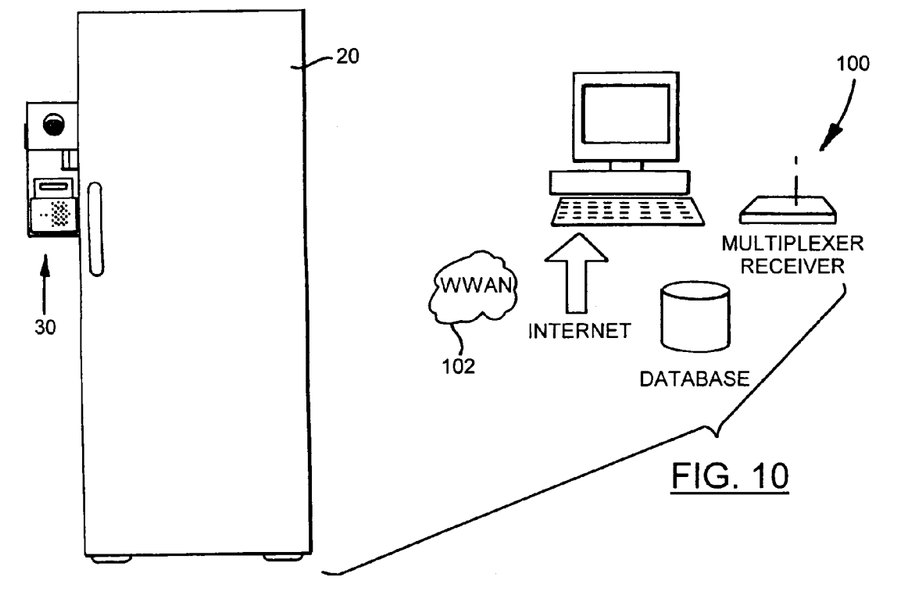
FIG. 10 is a schematic view of an inventory-tracking system including an inventory-tracking unit that communicates with a remote site over a wireless wide area network.
Figure 12:
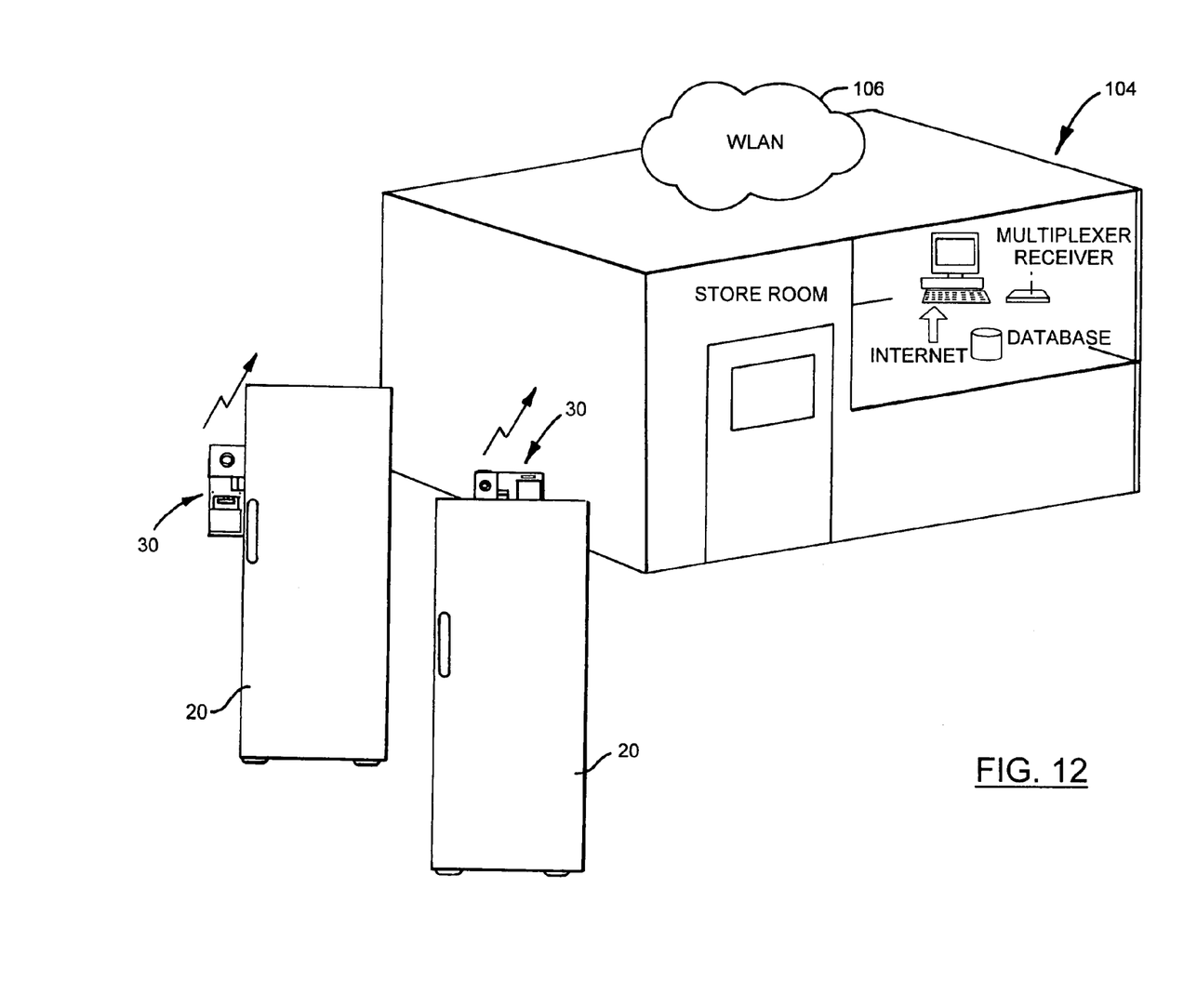
FIG. 12 is a schematic view of an inventory-tracking system including inventory-tracking units that communicate with a computer room over a wireless local area network.

After a user has completed a transaction with the refrigeration unit 20, the CPU 62 conveys the scanned barcode information to a remote site over a wireless communication link via the radio interface 70 and one of the transceivers 74 or 76. In the scenario shown in FIG. 10, the inventory-tracking unit 30 conveys the transaction to a remote site 100 over a wireless wide area network 102 via radio interface 70 and WAN transceiver 74. In the scenario shown in FIG. 12, inventory-tracking units 30 convey transactions to a computer room 104 over a wireless local area network 106 via radio interfaces 70 and LAN transceivers 76.

At the remote site, the received scanned barcode data is stored in a database so that an accurate real-time status of the inventory within the refrigeration unit 20 can be maintained. The maintenance of accurate inventory information allows useful sales reports to be generated and allows replenishment schedules to be adjusted to conform to inventory demand. Generated reports are posted on encrypted web pages that can be accessed by authorized users via Internet connections.

Depending on the environment, the scanned barcode data may be used to debit an account associated with the user. In this case, when the debit value of the account reaches a threshold level, the remote site generates a request for funds to zero the debit value. In this manner, the access card functions as both an access and debit card i.e. similar to a smart card.

If at any time, the temperature within the refrigeration unit rises above the threshold temperature as detected by the thermistor, the internal sensor antenna in the refrigeration unit 20 signals the inventory-tracking unit 30. In response, the CPU 62 generates an alarm signal that is used to sound siren 56 and records the alarm event. The CPU 62 also conveys the alarm event to the remote site over the wireless communications link so that the alarm event can be recorded. The CPU 62 also generates and records an alarm event when the door of the refrigeration unit 20 is left open for an extended period of time above a threshold and when the compressor of the refrigeration unit is believed to be approaching its service life. These alarm events are also recorded and conveyed to the remote site over the wireless communications link. In this manner service personnel can be quickly dispatched.

If desired, since the internal sensor antenna detects when items are placed into the refrigeration unit 20, the inventory-tracking unit 30 can be programmed to maintain an item count during restocking and convey the item count to the remote site providing for complete inventory control.

FIGS. 1 and 11 show a small number of inventory-tracking units 30 communicating with a remote site. Those of skill in the art will appreciate that this is for illustrative purposes only. In a typical environment, the remote site recieves transactions from a significant number of geographically distributed inventory-tracking units 30. Also, the inventory-tracking units may be used with other types of storage units such as for example vending machines and the like. In the case of vending machines that securely hold items, the requirement for a door locking mechanism is obviated.

Although embodiments of the present invention have been described, those of skill in the art will appreciate that variations and modifications may be made without departing from the spirit and scope thereof as defined by the appended claims.

What is claimed is:

1. A refrigeration unit for medical items, said refrigeration unit comprising:
   a refrigerated storage chamber in which medical items are held;
   at least one door mounted on said chamber, said door being moveable between a closed condition in which said chamber is sealed and an open condition where said medical items are openly accessible to users;
   a card reader to read an access card issued to an authorized user;
   a sensor associated with said storage chamber for automatically sensing removal of each item from said storage chamber and for generating first item identification data for each removed item;
   a scanner external of said storage chamber for subsequently reading data recorded on each item after the item has been removed from said storage chamber and for generating second item identification data;

a processor configured to communicate with said card reader, sensor and scanner, said processor configured to compare the first item identification data generated by the sensor for each removed item and the second item identification data read by the scanner from the same removed item to detect coincidence, said processor configured to generate a transaction upon coincidence of said first item identification data and said second item identification data; and a communications interface to transmit said transaction to a remote computing site.

2. The refrigeration unit of claim 1 wherein said communications interface configured to transmit said transaction over a wireless communications link.

3. The refrigeration unit of claim 1 wherein said scanner is a barcode scanner.

4. The refrigeration unit of claim 1 wherein said card reader configured to read a magnetic stripe on said access card.

5. The refrigeration unit of claim 1 further including a housing accommodating said card reader, scanner, processor and communications interface, said housing being coupled to said storage chamber.

6. The refrigeration unit of claim 5 further comprising a locking mechanism acting between said storage chamber and said door to maintain said door in said closed condition and inhibit said door from being moved to said open condition when in an engaged state, said locking mechanism being conditioned by said processor to a disengaged state to allow said door to be moved to said open condition to permit user access to items held in said storage chamber when a valid access card is read by said card reader.

7. The refrigeration unit of claim 6 wherein said processor is configured to communicate with at least one diagnostic sensor associated with said storage chamber, said processor is configured to transmit an alarm event to said remote computing site in response to an alarm condition signal received from said at least one diagnostic sensor.

8. The refrigeration unit of claim 7 wherein said at least one diagnostic sensor comprises a temperature sensor is configured to monitor the temperature within said storage chamber and is configured to generate said alarm condition signal when the temperature within said storage chamber exceeds a threshold.

9. An inventory-tracking system comprising:
a remote computing site; and
at least one refrigeration unit for medical items, said refrigeration unit including,
a refrigerated storage chamber in which medical items are held;
at least one door mounted on said chamber, said door being moveable between a closed condition in which said chamber is sealed and an open condition where said medical items are openly accessible to users;
a card reader to read an access card issued to an authorized user;
a sensor associated with said storage chamber for automatically sensing removal of each item from said storage chamber and for generating first item identification data for each removed item;
a scanner external of said storage chamber for subsequently reading data recorded on each item after the item has been removed from said storage chamber and for generating second item identification data;
a processor configured to communicate with said card reader, sensor and scanner, said processor configured to compare the first item identification data generated by the sensor for each removed item and the second item identification data read by the scanner from the same removed item to detect coincidence, said processor configured to generate a transaction upon coincidence of said first item identification data and said second item identification data; and
a communications interface to transmit said transaction to said remote computing site.

10. The inventory-tracking system of claim 9 comprising a plurality of refrigeration units at geographically spaced locations.

11. The inventory-tracking system of claim 10 wherein said refrigeration units are configured to communicate with said remote computing site over a wireless wide area network.

12. The inventory-tracking system of claim 10 wherein said refrigeration units are configured to communicate with said remote computing site over a wireless local area network.

13. The inventory-tracking system of claim 9 wherein said scanner is a barcode scanner.

14. The inventory-tracking system of claim 13 wherein said card reader is configured to read a magnetic stripe on said access card.

15. The inventory-tracking system of claim 13 wherein said at least one refrigeration unit further comprises a housing accommodating said card reader, scanner, processor and communications interface, said housing being coupled to said storage chamber.

16. The inventory-tracking system of claim 15 wherein said at least one refrigeration unit further comprises a locking mechanism acting between said storage chamber and said door to maintain said door in said closed condition and inhibit said door from being moved to said open condition when in an engaged state, said locking mechanism being conditioned by said processor to a disengaged state to allow said door to be moved to said open condition to permit access to items held in said storage unit when a valid access card is read by said card reader.

17. The inventory-tracking system of claim 16 wherein said processor is configured to communicate with at least one diagnostic sensor associated with said storage chamber, said processor is configured to transmit an alarm event to said remote computing site in response to an alarm condition signal received from said at least one diagnostic sensor.

18. The inventory-tracking system of claim 17 wherein said at least one diagnostic sensor comprises a temperature sensor is configured to monitor the temperature within said storage chamber and is configured to generateing said alarm condition signal when the temperature within said storage chamber exceeds a threshold.

19. The refrigeration unit of claim 6 wherein said processor is configured to condition said card reader to lock said access card therein until the first item identification data is coincident with said second item identification data.

20. The refrigeration unit of claim 6 wherein said scanner is enabled by said processor upon removal of items from said storage chamber and the subsequent movement of said door from said open condition to said closed condition.

21. The refrigeration unit of claim 6 wherein said processor is configured to monitor the elapsed time said door remains in said open condition and is configured to generate an alarm event when the elapsed time exceeds a threshold.

22. The inventory-tracking system of claim 16 wherein said processor is configured to condition said card reader to lock said access card therein until the first item identification data is coincident with said second item identification data.

23. The inventory-tracking system of claim 16 wherein said processor is configured to monitor the elapsed time said door remains in said open condition and is configured to generate an alarm event when the elapsed time exceeds a threshold.

24. A dispensing system comprising:
- a refrigerated storage unit holding a plurality of medical items, said items being openly accessible to a user authorized to access said storage unit when a door of said storage unit is moved from a closed condition to an open condition;
- a card reader to read an access card issued to an authorized user;
- a sensor associated with said storage unit for automatically sensing removal of each item from said storage unit and for generating first item identification data for each removed item;
- a scanner external of said storage unit for subsequently reading data recorded on each item after the item has been removed from said storage unit and for generating second item identification data;
- a processor is configured to communicate with said card reader, sensor and scanner, said processor is configured to compare the first item identification data generated by the scanner for each removed item and the second item identification data read by the scanner from the same removed item to detect coincidence, said processor is configured to generate a transaction upon coincidence of said first item identification data and said second item identification data; and
- a communications interface to transmit said transaction to a remote computing site.

* * * * *